United States Patent [19]

Haber

[11] Patent Number: 4,590,205
[45] Date of Patent: May 20, 1986

[54] ANTIINFLAMMATORY AND/OR ANALGESIC 2,3-DIARYL-5-HALO THIOPHENES

[75] Inventor: Stephen B. Haber, Wilmington, Del.

[73] Assignee: E. I. Du Pont de Nemours and Company, Wilmington, Del.

[21] Appl. No.: 570,450

[22] Filed: Jan. 17, 1984

Related U.S. Application Data

[63] Continuation of Ser. No. 354,300, Mar. 3, 1982, abandoned.

[51] Int. Cl.$^4$ .................... A61K 31/38; A61K 31/44
[52] U.S. Cl. ................................. 514/438; 514/333; 514/336; 549/80; 549/62; 546/256; 546/284
[58] Field of Search .................... 549/80, 62; 546/256, 546/284; 424/263, 275; 514/438, 333, 336

[56] References Cited

U.S. PATENT DOCUMENTS

| | | | |
|---|---|---|---|
| 2,625,553 | 1/1953 | Pines et al. | 260/332.5 |
| 2,639,286 | 5/1953 | Mavity | 260/329 |
| 4,174,405 | 11/1979 | Relyea et al. | 424/275 |
| 4,302,461 | 11/1981 | Cherkofsky | 424/275 |
| 4,381,311 | 4/1983 | Haber . | |

Primary Examiner—Alan Siegel

[57] ABSTRACT

Certain 2,3-diaryl-5-halo thiophenes are useful in the treatment of inflammation and/or pain.

16 Claims, No Drawings

ANTIINFLAMMATORY AND/OR ANALGESIC 2,3-DIARYL-5-HALO THIOPHENES

This application is a continuation of Ser. No. 354,300 filed 3/3/82 now abandoned.

BACKGROUND OF THE INVENTION

This invention relates to thiophene derivatives, pharmaceutical compositions containing them and methods of using them to treat inflammation and/or pain in mammals. More particularly, this invention relates to antiinflammatory and/or analgesic 2,3-diaryl-5-halo thiophenes.

Compounds of this general type are known in the art, but not as analgesic or antiinflammatory agents. A number of references including J. L. Melles and H. J. Backer, *Rec. trav. chim.*, 72, 314 (1953) and S. Hauptmann and E.-M. Werner, *J. prakt. Chem.*, 314, 499 (1972) disclose the preparation of 2,3-diphenylthiophene.

Melles and Backer, op. cit., describe the preparation of 2-bromo-3,4-diphenylthiophene; 4,5-dibromo-2,3-diphenylthiophene; 3,5-dibromo-2,4-diphenylthiophene and 3,4-dibromo-2,5-diphenylthiophene. U.S. Pat. No. 4,302,461 describes the use of 5-bromo-2,3-diarylthiophenes as intermediates. No biological activity is reported for any of these compounds. U.S. Pat. No. 4,174,405 describes 2-halo-3,5-diarylthiophenes and their use as acaricides.

There is a continuing need for safe and effective antiinflammatory agents. Inflammation is a disease process characterized by redness, fever, swelling, and pain. Arthritis, in its various forms, is the most prevalent, chronic, and severe of the inflammatory diseases. Traumatic injury and infection also involve inflammation, and antiinflammatory drugs are often used in their treatment. The usefulness of most commercial antiinflammatories is limited because of toxicity and adverse side-effects. Many produce gastric irritation and other effects, such as changes in blood cells and central nervous system. Adrenocortical steroids produce gastric irritation and suppression of normal adrenal function.

The present invention results from efforts to develop new antiarthritic compounds with good antiinflammatory activity and minimal side effects that could be more effective in treating arthritis than presently available drugs.

In addition to antiinflammatory properties, some compounds of this invention have demonstrated analgesic activity in a test procedure. This additional property is desirable in treatment of arthritis or related diseases; however, such compounds can be employed solely to alleviate pain.

SUMMARY OF THE INVENTION

It has been found that compounds of Formula I possess activity as antiarthritic agents and/or analgesic agents.

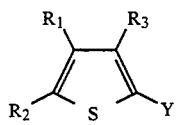
(I)

where
$R_1$ and $R_2$ are independently pyridyl or

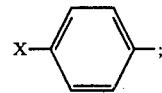

X is H, F, Cl, $C_1$-$C_2$ alkyl, $C_1$-$C_2$ alkoxy, $R_4S(O)_n$, $R_4R_5N$ or $NO_2$;
n is 0, 1 or 2;
$R_3$ is H or $C_1$-$C_2$ alkyl;
$R_4$ and $R_5$ are independently $C_1$-$C_2$ alkyl;
and
Y is F, Cl, Br or I; provided that,
(a) when Y is Br or I, then one of $R_1$ and $R_2$ is other than phenyl or 4-chlorophenyl; and
(b) when Y is Br or I and one of $R_1$ and $R_2$ is 4-chlorophenyl, then the other of $R_1$ and $R_2$ is other than 4-fluorophenyl; or
a pharmaceutically suitable salt thereof when $R_1$ and $R_2$ are independently pyridyl or when X is $R_4R_5N$.

This invention therefore relates to novel compounds of Formula I where Y, is F, Cl or I, to pharmaceutical compositions containing such novel compounds, and to the method of using all compounds of Formula I in treating inflammation and/or pain in mammals.

Preferred, for reasons of high activity and/or ease of synthesis, are those compounds of Formula I
where,
$R_3$ is H and, independently:
$R_1$ and $R_2$ are independently

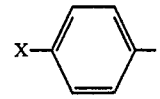

where
X is F, $C_1$-$C_2$ alkyl, $C_1$-$C_2$ alkoxy or $R_4S(O)_n$; or
Y is Br or Cl.

More preferred, for reasons of high acitivity and/or ease of synthesis, are those compounds
where:
$R_1$ and $R_2$ are independently

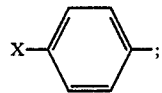

X is F, $CH_3$, $OCH_3$ or $CH_3S(O)_n$;
$R_3$ is H; and
Y is Br or Cl.
Most preferred are those compounds
where:
$R_1$ and $R_2$ are independently

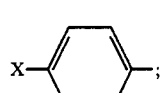

X is F or $CH_3S(O)_n$;
$R_3$ is H; and
Y is Br.
Specifically preferred are the following compounds:

5-bromo-3-(4-fluorophenyl)-2-(4-methylthiophenyl)thiophene;

5-bromo-2-(4-fluorophenyl)-3-(4-methylthiophenyl)thiophene; and 5-bromo-3-(4-fluorophenyl)-2-(4-methylsulfonylphenyl)thiophene.

DETAILED DESCRIPTION

Synthesis

The compounds of the invention may be prepared by the reaction of a source of positive halogen with a 2,3-diaryl thiophene. When Y=I, this reaction is conveniently performed using iodine in a solvent such as methylene chloride in the presence of mercuric oxide. When Y=Br, this reaction is conveniently performed using bromine in a solvent such as methylene chloride, acetic acid or their admixture. When Y=Cl, this reaction is conveniently performed using chlorine or N-chlorosuccinimide in a solvent such as methylene chloride, acetic acid or their admixture. When Y=F, this reaction is conveniently performed by first metallating the thiophene with a strong base such as n-butyl lithium in a solvent such as tetrahydrofuran and then treating the reaction mixture with a reagent such as perchloroyl fluoride.

The 2,3-diaryl thiophene can be prepared either by methods known in the art, for example, those in the previously cited Melles et al. and Hauptmann et al. references, or by methods analogous to those known procedures.

Compounds of this invention where $R_1$ and/or $R_2$ are pyridyl or are phenyl substituted with $NR_4R_5$ form salts which are within the scope of this invention. Pharmaceutically suitable salts and their preparation are well known to those skilled in pharmaceuticals. They include pharmaceutically suitable acid addition salts, preferably formed from mineral acids, and include hydrochloride, nitrate and sulfate.

The compounds of the invention and their synthesis are further illustrated by the following examples. All temperatures are in degrees Centigrade.

EXAMPLE 1

5-Bromo-2,3-bis(4-fluorophenyl)thiophene

A solution of 2,3-bis(4-fluorophenyl)thiophene (13.6 g, 50 mmole) in 120 ml methylene chloride and 150 ml acetic acid was cooled to ~5° and treated with bromine (2.8 ml, 55 mmole). After 4 hours, the reaction mixture was concentrated in vacuo. The residue was dissolved in ethyl acetate and washed with saturated aqueous sodium bicarbonate and brine, dried and concentrated in vacuo. Recrystallization from ethanol gave the title compound (14.7 g), m.p. 91°–93°.

NMR spectral data from a similar preparation were consistent with the assigned structure.

MS 350, 352 (M+).

EXAMPLE 2

5-Chloro-2,3-bis(4-methoxyphenyl)thiophene

A solution of N-chlorosuccinimide (2.92 g, 22 mmole) in 50 ml methylene chloride was added to a solution of 2,3-bis(4-methoxyphenyl)thiophene (5.92 g, 20 mmole) in 70 ml methylene chloride and 75 ml acetic acid. After 45 minutes at room temperature, the reaction mixture was heated at reflux for 18 hours. The cooled reaction mixture was then concentrated in vacuo.

The residue was dissolved in ethyl acetate, washed with saturated aqueous sodium bicarbonate and brine, dried and concentrated in vacuo. Recrystallization from methanol gave the title compound (4.27 g), m.p. 89°–92°. Infrared and NMR spectra were consistent with the assigned structure.

MS 330, 332 (M+), 315, 317 (M-CH$_3$).

EXAMPLE 3

5-Iodo-2,3-bis(4-methoxyphenyl)thiophene

A solution of 2,3-bis(4-methoxyphenyl)thiophene (5.92 g, 20 mmole) in 70 ml methylene chloride was cooled in an ice bath and treated in portions with iodine (5.6 g, 20 mmole) and red mercuric oxide (4.32 g, 20 mmole). The reaction mixture was stirred at room temperature for 4 hours and then treated with additional portions of iodine (2.8 g, 10 mmole) and mercuric oxide (2.16 g, 10 mmole). After 2 hours additional, the reaction mixture was filtered through a celite pad.

The filtrate was diluted with methylene chloride, washed with 10% aqueous sodium thiosulfate and brine, dried and concentrated in vacuo. Recrystallization from methanol gave the title compound (6.9 g), m.p. 83°–87°. Infrared and NMR spectra were consistent with the assigned structure.

MS 422 (M+), 407 (M-CH$_3$).

The following compounds can be prepared following procedures analogous to those outlined above and illustrated in the preceeding examples.

TABLE I

| Ex. | $R_1$ | $R_2$ | $R_3$ | Y | m.p. (°C.) |
|---|---|---|---|---|---|
| 1 | 4-F$\phi$ | 4-F$\phi$ | H | Br | 91–93° |
| 2 | 4-CH$_3$O$\phi$ | 4-CH$_3$O$\phi$ | H | Cl | 89–92° |
| 3 | 4-CH$_3$O$\phi$ | 4-CH$_3$O$\phi$ | H | I | 83–87° |
| 4 | 4-CH$_3$O$\phi$ | 4-CH$_3$O$\phi$ | H | F | |
| 5 | 4-F$\phi$ | 4-CH$_3$S$\phi$ | H | Br | 113–116° |
| 6 | 4-CH$_3$S$\phi$ | 4-F$\phi$ | H | Br | 75–78° |
| 7 | 4-CH$_3\phi$ | 4-CH$_3\phi$ | H | Br | 100–103° |
| 8 | 4-CH$_3$O$\phi$ | 4-CH$_3$S$\phi$ | H | Br | 92–94° |
| 9 | 4-F$\phi$ | 4-CH$_3$SO$_2\phi$ | H | Br | 141–145° |
| 10 | 4-F$\phi$ | 4-CH$_3$SO$_2\phi$ | H | Cl | 138–140° |
| 11 | 4-CH$_3$SO$_2\phi$ | 4-F$\phi$ | H | Cl | |
| 12 | 4-F$\phi$ | 4-C$_2$H$_5$S$\phi$ | H | Br | |
| 13 | $\phi$ | 4-CH$_3$S$\phi$ | H | Br | |
| 14 | 4-Cl$\phi$ | 4-CH$_3$S$\phi$ | H | Br | |
| 15 | 4-F$\phi$ | 4-CH$_3$S$\phi$ | CH$_3$ | Br | |
| 16 | 4-(CH$_3$)$_2$N$\phi$ | 4-CH$_3$S$\phi$ | H | Br | |
| 17 | 4-F$\phi$ | 4-NO$_2\phi$ | H | Br | |
| 18 | 4-CH$_3$S$\phi$ | 4-F$\phi$ | H | F | |
| 19 | 4-CH$_3$SO$_2\phi$ | 4-F$\phi$ | H | F | |
| 20 | 4-C$_2$H$_5\phi$ | 4-C$_2$H$_5\phi$ | H | Br | |
| 21 | 4-C$_2$H$_5$O$\phi$ | 4-C$_2$H$_5$O$\phi$ | H | Br | |
| 22 | 4-(C$_2$H$_5$)$_2$N$\phi$ | 4-CH$_3$S$\phi$ | H | Br | |
| 23 | 4-F$\phi$ | 4-CH$_3$S$\phi$ | C$_2$H$_5$ | Br | |
| 24 | 3-pyridyl | 4-CH$_3$S$\phi$ | H | Br | |

($\phi$ = phenyl)

Dosage Forms

The antiinflammatory and/or analgesic agents of this invention can be administered to treat inflammation and/or relieve pain by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl or propyl-paraben, and chlorobutanol.

Suitable pharmaceutical carriers are described in *Remington's Pharmaceutical Sciences*, E. W. Martin, a standard reference text in this field.

Useful pharmaceutical dosage forms for administration of the compounds of this invention can be illustrated as follows:

CAPSULES

A large number of unit capsules are prepared by filling standard two-piece hard gelatin capsules each with 50 milligrams of powdered active ingredient, 175 milligrams of lactose, 24 milligrams of talc, and 6 milligrams magnesium stearate.

SOFT GELATIN CAPSULES

A mixture of active ingredient in soybean oil is prepared and injected by means of a positive displacement pump into gelatin to form soft gelatin capsules containing 50 milligrams of the active ingredient. The capsules are washed in petroleum ether and dried.

TABLETS

A large number of tablets are prepared by conventional procedures so that the dosage unit is 50 milligrams of active ingredient, 6 milligrams of magnesium stearate, 70 milligrams of microcrystalline cellulose, 11 milligrams of cornstarch and 225 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol and water. The solution is sterilized by commonly used techniques.

SUSPENSION

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

INJECTABLE

A parenteral composition suitable for administration by injection is prepared by dissolving 1% by weight of active ingredient in sodium chloride injection U.S.P. XX and adjusting the pH of the solution to between 6 and 7. The solution is sterilized by commonly used techniques.

USE

To detect and compare the antiinflammatory activities of compounds in this series and standard drugs, a test was used based on a standard model of arthritis for which there is good correlation with human efficacy. The model is adjuvant-induced arthritis in rats. *Federation Proceedings*, Vol. 32, No. 2, 1973 "Models Used for the Study and Therapy of Rheumatoid Arthritis''—Symposium of the American Society for Pharmacology And Experimental Therapeutics—states "The rat polyarthritis produced by intradermal injection of a suspension of *Mycobacterium tuberculosis* in mineral oil (adjuvant) has been used extensively for the screening of drugs of potential use in rheumatoid arthritis."

ESTABLISHED ADJUVANT-INDUCED ARTHRITIS IN RATS

Charles River Lewis male rats (130-150 grams) are injected subcutaneously in the plantar area of the right hind paw with 0.1 ml of adjuvant (Difco heat-killed, lyophilized *Mycobacterium butyricum* suspended in mineral oil 5 mg/ml). 20 Non-arthritic controls are injected with mineral oil. The animals are held for 2 weeks to allow development of arthritis. Paw volumes (uninjected, left hind paw) are measured and the adjuvant-injected rats are culled and distributed to treatment groups of 10 of equal disease severity. Non-arthritic controls are distributed to 2 groups of 10. The rats are given oral doses of compound or PVA-Acacia (Polyvinyl Alcohol 1%, Gum acacia, U.S.P. 5%, Methylparaben 0.5%) (10 ml/kg) by gavage on that day and on the 6 following days. One day after the last dose the paw volumes (uninjected, left hind paw) are measured using a Ugo Basile Volume Differential Meter Model 7101.

$$\frac{\text{Arthritic Control} \quad \text{Treatment Group}}{\text{Arthritic Control} \quad \text{Non-Arthritic Control}} \times 100 =$$
$$\text{Mean Paw Volume (ml)} - \text{Mean Paw Volume (ml)}$$

% Decrease from Control Mean Paw Volume.

Dose-response regression lines of the percent decrease are plotted on semi-log paper by visual fit and the ED50% decrease from control paw volume is determined by inspection. Data for some of the compounds in this invention are summarized in Tables II.

Compounds from this series were also compared to indomethacin, phenylbutazone, ibuprofen, and aspirin.

PHENYLQUINONE WRITHING TEST

A standard procedure for detecting and comparing the analgesic activity of compounds in this series for which there is a good correlation with human efficacy is the standard phenylquinone writhing test modified from Siegmund, et al., *Proc. Soc. Exp. Biol. Med.*, 95, 729 (1957). A test compound suspended in 1% methylcellulose was given orally to fasted (17-21 hours) female white mice, 5-20 animals per double blind test. Aqueous (0.01% phenyl-p-benzoquinone) phenylquinone, 0.20 ml per mouse, was injected intraperitoneally 6 minutes before observations were begun. At an appropriate time after the oral administration of the test compound, the mice were observed for 10 minutes for a characteristic stretching or writhing syndrome which is indicative of pain induced by phenylquinone. The effective analgesic dose for 50% of the mice ($ED_{50}$) was calculated by the moving average method of Thompson, W. R., *Bact. Rev.*, 11, 115-145 (1947); the time of peak activity was determined for many of the compounds. Data for some of the compounds is summarized in Table II together with data for some standard analgetic antiinflammatory drugs.

TABLE II

| Example | Adjuvant Arthritis $ED_{50}$ (mg/kg) | PQW $ED_{50}$ (mg/kg) |
|---|---|---|
| 1 | >60 | 6.8 |
| 2 | 4.5 | 2.1 |
| 3 | 46% @ 81[1] | <15 |
| 5 | 1.4 | >108 |
| 6 | 0.25 | >108 |
| 7 | >81 | 2.9 |
| 8 | 2.9 | <15 |
| 9 | 0.4 | >108 |
| Indomethacin | 0.3 | 0.35 |
| Phenylbutazone | 10 | 80 |
| Ibuprofen | 100 | 10 |
| Aspirin | 305 | 135 |

[1]% Decrease from control paw volume at indicated daily dose.

What is claimed is:

1. A method of treating inflammation, pain or both in a mammal which comprises administering to the mammal an effective antiinflammatory or analgesic amount of at least one compound of the formula:

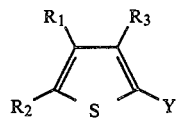

where
$R_1$ and $R_2$ are independently pyridyl or

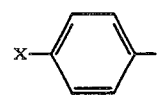

where
X is H, F, Cl, $C_1$-$C_2$ alkyl, $C_1$-$C_2$ alkoxy, $R_4S(O)_n$, $R_4R_5N$ or $NO_2$;
n is 0, 1 or 2;
$R_3$ is H or $C_1$-$C_2$ alkyl;
$R_4$ and $R_5$ are independently $C_1$-$C_2$ alkyl; and
Y is F, Cl, Br or I; provided that,
(a) when Y is Br or I, then one of $R_1$ and $R_2$ is other than phenyl or 4-chlorophenyl; and
(b) when Y is Br or I and one of $R_1$ and $R_2$ is 4-chlorophenyl, then the other of $R_1$ and $R_2$ is other than 4-fluorophenyl;
or a pharmaceutically suitable salt thereof when $R_1$ and $R_2$ are independently pyridyl or when X is $R_4R_5N$.

2. The method of claim 1 where $R_3$ is H and $R_1$ and $R_2$ are independently

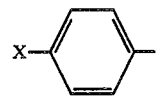

where X is F, $C_1$-$C_2$ alkyl, $C_1$-$C_2$ alkoxy or $R_4S(O)_n$.

3. The method of claim 1 where $R_3$ is H and Y is Br or Cl.

4. The method of claim 2 where X is F, $CH_3$, $OCH_3$ or $CH_3S(O)_n$ and Y is Br or Cl.

5. The method of claim 4 where X is F or $CH_3S(O)_n$ and Y is Br.

6. The method of claim 5 where the compound is 5-bromo-3-(4-fluorophenyl)-2-(4-methylthiophenyl)thiophene.

7. The method of claim 5 where the compound is 5-bromo-2-(4-fluorophenyl)-3-(4-methylthiophenyl)thiophene.

8. The method of claim 5 where the compound is 5-bromo-3-(4-fluorophenyl)-2-(4-methylsulfonylphenyl)thiophene.

9. A pharmaceutical composition consisting essentially of a suitable pharmaceutical carrier for oral or parenteral administration and approximately 0.5-95% by weight of an effective antiinflammatory or analgesic amount of a compound of the formula

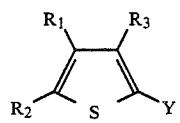

where
$R_1$ and $R_2$ are independently pyridyl or

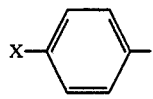

where
X is H, F, Cl, $C_1$–$C_2$ alkyl, $C_1$–$C_2$ alkoxy, $R_4S(O)_n$, $R_4R_5N$ or $NO_2$;
n is 0, 1 or 2;
$R_3$ is H or $C_1$–$C_2$ alkyl;
$R_4$ and $R_5$ are independently $C_1$–$C_2$ alkyl; and
Y is F, Cl, Br or I:
provided that,
(a) when Y is I, then one of $R_1$ and $R_2$ is other than phenyl or 4-chlorophenyl; and
(b) when Y is I and one of $R_1$ and $R_2$ is 4-chlorophenyl, then the other of $R_1$ and $R_2$ is other than 4-fluorophenyl;
or a pharmaceutically suitable salt thereof when $R_1$ and $R_2$ are independently pyridyl or when X is $R_4R_5N$.

10. The composition of claim 9 where $R_3$ is H and $R_1$ and $R_2$ are independently

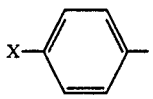

where X is F, $C_1$–$C_2$ alkyl, $C_1$–$C_2$ alkoxy or $R_4S(O)_n$.

11. The composition of claim 9 where $R_3$ is H and Y is Br or Cl.

12. The composition of claim 10 where X is F, $CH_3$, $OCH_3$ or $CH_3S(O)_n$ and Y is Br or Cl.

13. The composition of claim 12 where X is F or $CH_3S(O)_n$ and Y is Br.

14. The composition of claim 13 where the compound is 5-bromo-3-(4-fluorophenyl)-2-(4-methylthiophenyl)-thiophene.

15. The composition of claim 13 where the compound is 5-bromo-2-(4-fluorophenyl)-3-(4-methylthiophenyl)-thiophene.

16. The composition of claim 13 where the compound is 5-bromo-3-(4-fluorophenyl)-2-(4-methylsulfonylphenyl)thiophene.

* * * * *